United States Patent [19]
Hirschman

[11] Patent Number: 5,807,840
[45] Date of Patent: Sep. 15, 1998

[54] METHOD FOR TREATING CANINE DISTEMPER

[75] Inventor: Shalom Z. Hirschman, Riverdale, N.Y.

[73] Assignee: Advanced Viral Research Corp., Hallandale, Fla.

[21] Appl. No.: 963,849

[22] Filed: Nov. 4, 1997

[51] Int. Cl.$^6$ .................................................. A61K 31/70
[52] U.S. Cl. ........................ 514/44; 514/868; 424/1.17; 424/1.73; 424/159.1; 424/211.1; 424/213.1
[58] Field of Search ................... 514/44, 868; 424/1.17, 424/1.73, 159.1, 211.1, 213.1

[56] References Cited

PUBLICATIONS

Reynolds, Margaret R., Generalized Vaccinia, Symposium, pp. 5–6, 1960.
Kuckku, Morris E., Herpetic Diseases, Symposium, pp. 7–13, 1960.
Schaeffer, Oden A., Influenza, Symposium, pp. 15–21, 1960.
Seydel, Frank, Epidemic, Asian Influenza, Symposium, pp. 23–24 1960.
Cooke, Stanford B., Upper Respiratory Viral Manifestations, Clinical Symposium on Viral Diseases Demonstrating the Anti–viral Biotic Properties of the Drug Reticulose (Symposium), Sep., 1960, Miami Beach, Fla., pp. 25–32.
Medoff, Lawrence R.r., Infectious Mononucleosis, Symposium, pp. 33–37, 1960.
Anderson, Robert H., Encephalitis, Symposium, pp. 39–52, 1960.
Plucinski, Stanisloff J., Suspected Viral Varieties, Symposium, pp. 53–59, 1960.
Anderson, Robert H. and Thompson, Ralph M., Treatment of Viral Syndrome with a Lipoprotein–Nucleic Acid Compound (Reticulose), A Report of Five Cases, Virginia Medical Monthly, 84:347–353, 1957.
Reynolds, Margaret R., Generalized Vaccinia Successfully Treated With Lipoprotein–Nucleic Acid Complex (Reticulose), Archives of Pediatrics, 77:421–422, 1960.
Wegryn, Stanley P. Marks, Robert A. and Baugh, John R., Herpes Gestationis, A Report of 2 Cases, American Journal of Obstetrics and Gynecology, 79:812–814, 1960.
Catterall, R.A., Lumpur, Kuala, A New Treatment of Herpes Zoster, Vaccinia And Chicken Pox, J. Roy, Coll. Gen. Practit., 1970, 19, 182.
Chinnici, Angelo A., Reticulose in Treatment Aids patients, Personal Communication to William Bregman, Jul. 6, 1992.
Cott, Rafael A., Summary of 11 Cases of Viral Infections Treated with Reticulose, Private Communication with Advance Viral Research Corp., 1989.
Cohen, Matthew, The Efficacy of a Peptide–Nucleic Acid Solution (Reticulose) for the Treatment of Hepatitis A and Hepatitis B –a Preliminary Controlled Human Clinical Trial, J. Roy. Soc. Health, Dec., 1992, 266–270.
Mundschenk, David D., In Vitro Antiviral Activity of Reticulose vs Influenaz A, Personal Communication with William Bregman, May 1, 1990.
Resnick, Lionel, Anti–HIV in Vitro Activity of Two Samples of Peptide–nucleic Acid Solution, Personal Communication with Dr. Bernard Friedland, Dec. 22, 1989.
Friedland, Bernard, In Vitro Antiviral Activity of a Peptide––Nucleic Acid Solution Against the Human Immunodeficiency Virus and Influenza A Virus, J. Roy. Soc. Health, Oct. 1991, 170–171.
Brazier, Anne D., Method for in Vitro Antiviral Evaluation Human Immunodeficiency Virus (HIV), Personal Communication with Dr. Bernard Friedland, Oct. 4, 1989.
Behbehani, Abbas M., Haberman Sol and Race, George J, The Effect of Reticulose on Viral Infections of Experimental Animals, Southern Medical Journal, Feb., 1962, 185–188.
Treatment of Viral Diseases with A Lipo–protein Nucleic Acid Complex (Reticulose) –A Clinical Study, Scientific Exhibit: Virginia State Medical Society Meeting, Washington D.C., Nov., 1957.
Kempe, Henry C., Fulginiti, Vincent A., and Vincent, Leone St., Failure to Demonstrate Antiviral Activity of Reticulose, Diseases of Children, vol. 103, No. 5, 655–657, 1962.
Sanders, Murray, Controlled Animal Studies with Reticulose Illustrating the Interference of Lipoprotein–Nucleic Acid Complex in the Experimental Animal Infected with Human Pathogenic Viral Entities, Southern Medical Association Scientific Exhibit, Dallas, Texas, Nov., 1961.

*Primary Examiner*—James O. Wilson
*Attorney, Agent, or Firm*—Cohen, Pontani, Lieberman & Pavane

[57] ABSTRACT

The present invention discloses a method for treating patients having the CDV associated symptoms or animals carrying or infected by the canine distemper virus (CDV) or having antibodies against the CDV using Product R, a peptide-nucleic acid preparation.

12 Claims, No Drawings

METHOD FOR TREATING CANINE DISTEMPER

BACKGROUND OF THE INVENTION

1. Field of the Invention

The present invention relates to a method for using Product R as hereinafter defined to treat animals infected with canine distemper virus (CDV).

2. Description of the Related Art

Canine distemper was first described by Carre in 1905 as an infectious disease of young dogs associated with gastroenteritis, pneumonitis, conjunctivitis, and encephalomyelitis. Canine distemper was definitively shown to be of viral etiology in 1926, and the virus was isolated in primary canine kidney cells in 1959.

Canine distemper virus belongs to the family Paramyxoviridae and the subfamily Paramyxovirinae. The genome of the family Paramyziviridae is nonsegmented single-stranded RNA of negative polarity. The genome is approximately 15,500 nucleotides in length and contains a 3' extracistronic region of approximately 50 nucleotides known as the leader and a 5' extracistronic region of approximately 50 nucleotides known as the trailer. These control regions, which are essential for transcription and replication, flank the six genes. The coding capacity of the genome of Paramyxovirinae is extended by the use of overlapping reading frames in the P gene. For the Paramyxovirinae the P gene represents an extraordinary example of a virus compacting as much genetic information as possible into a small gene. The p gene gives rise to a plethora of polypeptide products by means of using overlapping reading frames and by a remarkable process of transcription known as RNA editing or pseudotemplate addition of nucleotides, the consequence of which is a reading frame shift on translation.

Canine distemper is a severe disease of canines, raccoons, ferrets, and seals with many similarities to measles, but direct infection of the CNS and neurologic disease is more common. The disease is spread by aerosol and characterized by fever, coryza, conjunctivitis, gastroenteritis, and pneumonitis. CDV appears first in bronchial lymph nodes and tonsils followed by a cell-associated viremia. Infection spreads to epithelial tissues and enters the brain by infecting endothelial cells or by infiltration of infected monocytes. Like measles, canine distemper is associated with profound short- and long-term immune suppression, and much of the mortality is due to secondary infections. In fact, early workers thought the disease was of bacterial etiology. Virus is cleared with the onset of the immune response in most animals, and clearance is correlated with production of antibodies to envelope proteins and with the appearance of lymphocyte-mediated cytotoxicity for infected cells.

Both dogs and ferrets may develop neurologic complications characterized by gait abnormalities and seizures. Neurologic disease is most common in young dogs. It can occur either early after infection or 3 to 4 weeks later. The late disease is often associated with infection of oligodendrocytes and demyelination.

Virus may persist in neurons and epidermal cells of the feet. Persistence of virus in these sites is thought to lead to old dog encephalitis and hard pad disease seen in middle-aged dogs. Some cases of old dog encephalitis have features in common with SSPE, such as defective virus with intranuclear inclusions in the CNS coexisting with high levels of antiviral antibody. In other cases virus can be isolated without concultivation, and the disease cannot be clearly distinguished from late-onset encephalitis.

Product R[1] emerged as an antiviral product in the 1930's. While it was originally believed to be a product composed of peptone, peptides and nucleic acids (fully defined hereafter), the precise composition remains unidentified. Nevertheless, Product R has demonstrated an ability to inhibit rapidly the course of several viral diseases. It is nontoxic, miscible with tissue fluids and blood sera and free from anaphylactogenic properties.

[1] The agent is known under the trademark "Reticulose", a trademark of Advanced Viral Research Corp.

Insofar as the applicant knows, Product R has never been used, nor suggested for treating animals having virus infections other than human. It is now discovered that Product R is useful in treating animals having CDV infections.

SUMMARY OF THE INVENTION

The object of this invention therefore is to provide a method for treating animals infected by canine distemper virus (CDV), or exhibiting CDV associated symptoms, or having antibodies against CDV, by administering parenterally to the animals Product R, an antiviral agent composed of peptides and nucleic acids.

More specifically, the present invention relates to a method for treating the identified animals by administering parenterally to the animals an effective CDV treatment amount of Product R from about 5 microliters to about 40 microliters per kilogram of body weight per day in a sterile injectable formulation.

Other objects and features of the present invention will become apparent from the following detailed description considered. It is to be understood, however, that the description is designed solely for purposes of example and not as a definition of the limits of the invention, for which reference should be made to the appended claims.

DETAILED DESCRIPTION OF THE PRESENTLY PREFERRED EMBODIMENTS

As used herein, Product R is the product produced according to either of the following methods.

Method I For Preparing Product R

Suspend about 35.0 g of casein, about 17.1 g of beef peptone, about 22.0 g of nucleic acid (RNA), about 3.25 g bovine serum albumin in about 2.5 liters of water for injection USP at about 3° to 7° C. in a suitable container and gently stir until all the ingredients have been properly wet. Carefully add while stirring about 16.5 g of sodium hydroxide (reagent grade ACS) and continue stirring until sodium hydroxide completely dissolved. Autoclave at about 9 lbs pressure and 200°–230° F. for a period of time until RNA is completely digested, for example, about 4 hours. At the end of the period, the autoclave is stopped and the reaction flask and contents are permitted to slowly cool to ambient temperature. Then cool for at least six hours at about 3°–8° C. The resulting solution is filtered through 2 micron and 0.45 micron filters using inert gas such as nitrogen or argon at low pressure (1–6 psi). In a similar manner the solution is filtered again through 0.2 micron pyrogen retention filters. The resulting filtrate is sampled and assayed for total nitrogen. A calculation is then performed to determine the quantity of cooled water for injection to be added to the filtrate to yield a diluted filtrate with a nitrogen content between about 165–210 mg/100 ml, the final volume is approximately 5 liters. The pH is then adjusted with either concentrated HCl (reagent grade ACS) or 1.0 normal NaOH to about 7.3–7.6 range. The diluted solution is then filtered again through 0.2 micron filters with inert gas at low pressure. The final filtrate is then filled and sealed into 2 ml glass ampules while in an inert gas atmosphere. The ampules are collected and autoclaved for final sterilization at 240 ° F. and 20 to 30 pounds pressure for about 30 minutes. Following the sterilization cycle, the ampules with Product R are cooled and washed.

All quantities are subject to plus or minus 2.5% variation for pH, volume, and analytical adjustments.

Method II For Preparing Product R

Suspend about 35.0 g of casein, about 17.1 g of beef peptone, about 22.0 g of nucleic acid (RNA), about 3.25 g bovine serum albumin in about 2.5 liters of water for injection USP at about 3° to 7° C. in a suitable container and gently stir until all the ingredients have been properly wet. Slowly add while stirring about 11.75 ml of hydrochloric acid (reagent grade ACS) and continue stirring until hydrochloric acid is completely dissolved. Autoclave at about 9 lbs pressure and 200°–230° F. for a period of time until RNA is completely digested, for example, about 4 hours. At the end of the period, the autoclave is stopped and the reaction flask and contents are permitted to slowly cool to ambient temperature. Then cool for at least six hours at about 3°–8° C. The resulting solution is filtered through 2 micron and 0.45 micron filters using inert gas such as nitrogen or argon at low pressure (1–6 psi). In a similar manner the solution is filtered again through 0.2 micron pyrogen retention filters. The resulting filtrate is sampled and assayed for total nitrogen. A calculation is then performed to determine the quantity of cooled water for injection to be added to the filtrate to yield a diluted filtrate with a nitrogen content between about 165–210 mg/100 ml, the final volume is approximately 5 liters. The pH is then adjusted with either concentrated HCl (reagent grade ACS) or 35% (w/v) of NaOH to about 7.3–7.6 range. The diluted solution is then filtered again through 0.2 micron filters with inert gas at low pressure. The final filtrate is then filled and sealed into 2 ml glass ampules while in an inert gas atmosphere. The ampules are collected and autoclaved for final sterilization at 240° F. and 20 to 30 pounds pressure for about 30 minutes. Following the sterilization cycle, the ampules with Product R are cooled and washed.

All quantities are subject to plus or minus 2.5% variation for pH, volume, and analytical adjustments.

For animals with the above CDV infections or CDV associated symptoms, or having antibodies against CDV, a suitable effective dose of Product R is in the range of from about 5 microliters to about 40 microliters per kilogram of body weight per day, preferably in the range of about 10 microliters to about 25 microliters per kilogram of body weight per day. Most preferably Product R is administered in an amount of about 30 microliters per kilogram of body weight per day for about one week, followed by about 15 microliters per kilogram of body weight per day in a sterile injectable formulation until the patient becomes asymptomatic or viral load becomes undetectable. The desired dose may be administered as two, three or more sub-doses at appropriate intervals, generally equally spread in time, throughout the day. Preferably, the full daily dose is administered in one administration.

Product R may be administered by any suitable injection route including, but not limited to intravenously, intraperitoneally, subcutaneously, intramuscularly, and intradermally, etc. The presently preferred route of administration is intramuscularly. It will be appreciated that the preferred route may vary with, for example, the condition and age of the recipient.

Product R may be used in therapy in conjunction with other medicaments including corticosteroid, gamma globulin, glucose, or vitamins, antiviral agents such as interferon or interleukin, etc.

While it is possible for Product R to be administered as part of a pharmaceutical formulation, it is preferable to present it alone, although it may be administered at about the same time as one or more other pharmaceuticals are independently administered. If Product R is administered as part of a pharmaceutical formulation, the formulations of the present invention comprise at least one administered ingredient, as above defined, together with one or more acceptable carriers thereof and optionally other therapeutic ingredients. The carrier(s) must be "acceptable" in the sense of being compatible with the other ingredients of the formulation and not deleterious to the recipient thereof. Preferably, Product R constitutes at least about 90% of such formulation by weight.

The formulations may conveniently be presented in unit-dose or multi-dose containers, e.g. sealed ampules and vials.

Preferred unit dosage formulations are those containing a daily dose or unit, daily sub-dose, or an appropriate fraction of the administered ingredient.

Thus, while there have been shown and described and pointed out fundamental novel features of the invention as applied to preferred embodiments thereof, it will be understood that various omissions and substitutions and changes in the form and details of the methods illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. It is the intention, therefore, to be limited only as indicated by the scope of the claims appended hereto.

I claim:

1. A method of treating an animal having a Canine Distemper Virus infection or symptoms associated with Canine Distemper Virus infections, comprising administering parenterally to said animal an effective Canine Distemper Virus treatment amount of Product R in a sterile injectable formulation.

2. The method of claim 1 in which an effective treatment amount of Product R is in a range from about 5 microliters to about 40 microliters per kilogram of body weight of said animal per day in a sterile injectable formulation.

3. The method of claim 1 in which an effective treatment amount of Product R is in a range from about 10 microliters to about 25 microliters per kilogram of body weight of said animal per day in a sterile injectable formulation.

4. The method of claim 1 in which an effective treatment amount of Product R is about 30 microliters per kilogram of body weight of said animal per day in a sterile injectable formulation for about one week, followed by about 15 microliters per kilogram of body weight per day in a sterile injectable formulation until said animal becomes asymptomatic or viral load becomes undetectable.

5. A method of treating an animal infected by Canine Distemper Virus, comprising administering parenterally to said animal an effective Canine Distemper Virus treatment amount of Product R in a sterile injectable formulation.

6. The method of claim 5 in which an effective treatment amount of Product R is in a range from about 5 microliters to about 40 microliters per kilogram of body weight of said animal per day in a sterile injectable formulation.

7. The method of claim 5 in which an effective treatment amount of Product R is in a range from about 10 microliters to about 25 microliters per kilogram of body weight of said animal per day in a sterile injectable formulation.

8. The method of claim 5 in which an effective treatment amount of Product R is about 30 microliters per kilogram of body weight of said animal per day in a sterile injectable formulation for about one week, followed by about 15 microliters per kilogram of body weight per day in a sterile injectable formulation until said animal becomes asymptomatic or viral load becomes undetectable.

9. A method of treating an animal having antibodies to the Canine Distemper Virus, comprising administering parenterally to said animal an effective Canine Distemper Virus treatment amount of Product R in a sterile injectable formulation.

10. The method of claim 9 in which an effective treatment amount of Product R is in a range from about 5 microliters to about 40 microliters per kilogram of body weight of said animal per day in a sterile injectable formulation.

11. The method of claim 9 in which an effective treatment amount of Product R is in a range from about 10 microliters to about 25 microliters per kilogram of body weight of said animal per day in a sterile injectable formulation.

12. The method of claim 9 in which an effective treatment amount of Product R is about 30 microliters per kilogram of body weight of said animal per day in a sterile injectable formulation for about one week, followed by about 15 microliters per kilogram of body weight per day in a sterile injectable formulation until said animal becomes asymptomatic or viral load becomes undetectable.

\* \* \* \* \*